United States Patent [19]

Favier et al.

[11] 4,374,837
[45] Feb. 22, 1983

[54] PIPERAZINE DERIVATIVES OF THEOBROMINE

[75] Inventors: Colette Favier, Neuilly-sur-Seine; Henri Pinhas, Paris; Serge Beranger, Bretigny-sur-Orge; Jean-Claude Pascal, Cachan, all of France

[73] Assignee: Laroche Navarron, S.A., Palo Alto, Calif.

[21] Appl. No.: 288,847

[22] Filed: Jul. 31, 1981

[51] Int. Cl.³ .................... A61K 31/52; C07D 473/10
[52] U.S. Cl. .............................. 424/253; 544/271; 544/272
[58] Field of Search ............... 544/271, 272; 424/253

[56] References Cited

U.S. PATENT DOCUMENTS 3,459,753  8/1969  Boltze et al. .................. 544/270
3,734,911  5/1973  Bestian .......................... 544/272

Primary Examiner—Paul M. Coughlan, Jr.
Attorney, Agent, or Firm—Tom M. Moran; Alan M. Krubiner

[57] ABSTRACT

New compounds of the formula

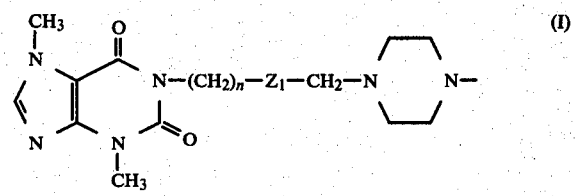

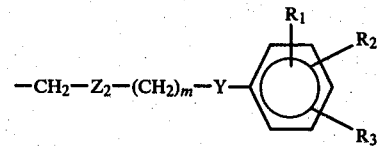

and the pharmaceutically acceptable acid addition salts thereof, wherein $Z_1$ and $Z_2$ are each independently selected from the group consisting of $CH_2$, CHOB and C=O, wherein B is selected from the group consisting of hydrogen and alkanoyl;

Y is oxygen or sulfur;

n is an integer from 0-4 but cannot be zero when $Z_1$ is CHOB;

m is an integer from 0-4 but cannot be zero when $Z_2$ is CHOB; and $R_1$, $R_2$ and $R_3$ are each independently hydrogen, halogen, hydroxy, trifluoromethyl, alkyl or alkoxy;

are antihistamines and are therefore useful in the treatment of respiratory diseases including asthma, hay fever, allergies and the common cold.

7 Claims, No Drawings

PIPERAZINE DERIVATIVES OF THEOBROMINE

BACKGROUND OF THE INVENTION

This invention relates to piperazines derivatives of theobromine and to their utility as treatment compounds for respiratory and allergic diseases.

Theobromine, itself, is well known as a duiretic, cardiac stimulant and smooth muscle relaxant and vasodilator. Addition of the piperazine containing substituent confers a range of pharmacologic activities which render the resulting compounds useful in the symptomatic treatment of asthma, hay fever and other respiratory diseases such as, for example, the common cold.

SUMMARY OF THE INVENTION

The present invention concerns novel compounds of the formula

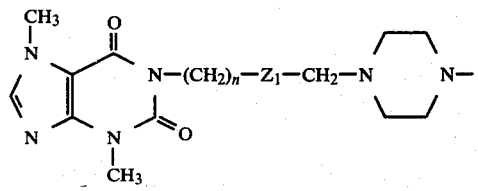

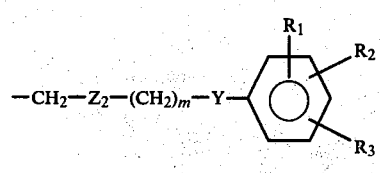

and the pharmaceutically acceptable acid addition salts thereof, wherein
- $Z_1$ and $Z_2$ are each independently selected from the group consisting of $CH_2$, CHOB and C=O, wherein B is selected from the group consisting of hydrogen and alkanoyl;
- Y is oxygen or sulfur;
- n is an integer from 0–4 but cannot be zero when $Z_1$ is CHOB;
- m is an integer from 0–4 but cannot be zero when $Z_2$ is CHOB; and
- $R_1$, $R_2$ and $R_3$ are each independently hydrogen, halogen, hydroxy, trifluoromethyl, alkyl or alkoxy.

In another aspect, this invention concerns pharmaceutical compositions containing the above compounds as active ingredients.

In a third aspect, the invention concerns a method for treating, or relieving the symptoms of, respiratory disorders using the above compounds or using pharmaceutical compositions containing them.

In a fourth aspect, the invention concerns processes for preparing these compounds.

DETAILED DESCRIPTION OF THE INVENTION

Definitions:

As used herein

"Alkyl" means a branched or unbranched saturated hydrocarbon chain containing 1-6 carbon atoms, such as methyl, ethyl, propyl, tert-butyl, n-hexyl and the like;

"Alkoxy" means —OR wherein R is alkyl as herein defined.

"Alkanoyl" means

wherein R is alkyl as defined herein.

"Halogen" means chloro, bromo or iodo.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

In the reaction schemes are shown herein below, and in the claims:

"ThB" represents the theobromin-1-yl moiety:

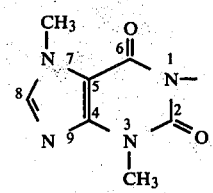

i.e. theobromine, which is linked to the remainder of the molecule through the ring nitrogen at position 1.

"X" represents a halogen atom; i.e. chloro, bromo or iodo; however, each X shown may be selected independently from this group;

"A" represents a moiety selected from the group consisting of $$-(CH_2)_{(n+2)}-X$$

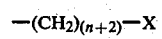

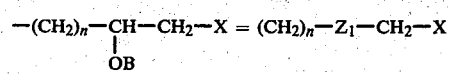

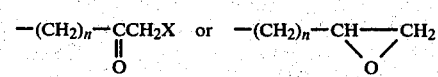

wherein n is as herein defined.

Process for Preparation

Reaction Schemes 1 and 2, shown below, are complementary processes for linking the two "halves" of the compounds of Formula I through the piperazine ring.

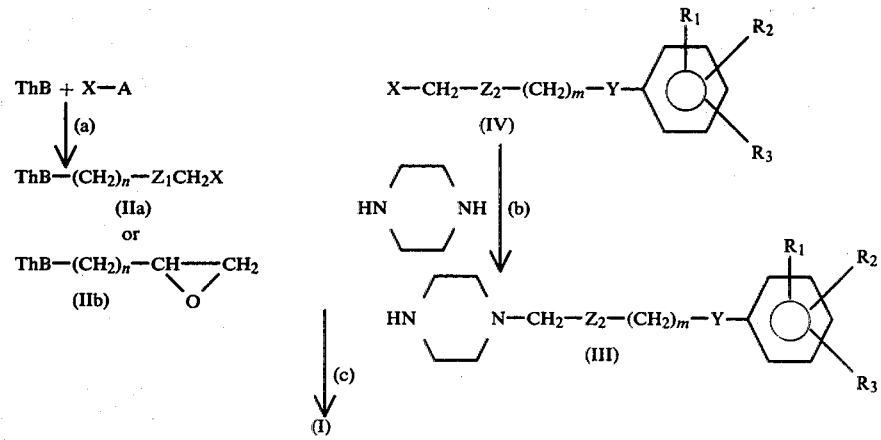

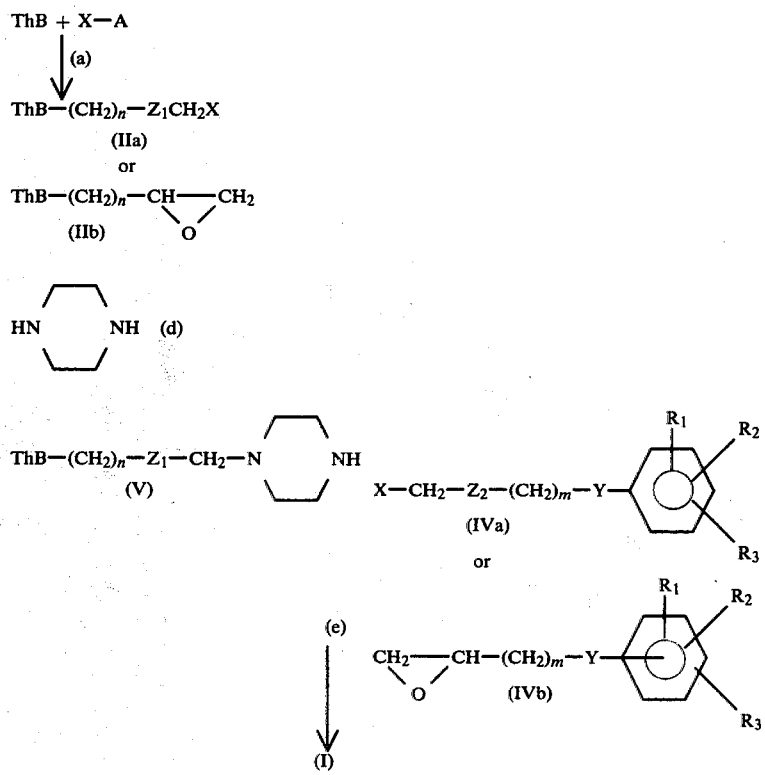

Reaction Scheme 2

In the reaction schemes shown, isolation and purification of the compounds and intermediates described, whether in the body of the specification, or examples, can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to a dryness, and the salts can be further purified by conventional methods.

The compounds of the present invention in which $Z_1$ and/or $Z_2$ is CHOB and which, therefore, contain at least one chiral center, may be prepared in either optically active form or as racemic mixtures. Unless otherwise specified, the compounds described herein are all in the racemic form. However, the scope of the subject invention herein is not to be considered limited to the racemic forms, but to encompass the individual optical isomers of the compounds.

In those embodiments where both $Z_1$ and $Z_2$ are chiral, diastereomeric forms also are possible. The invention herein includes mixtures of diastereomers as well as individual diastereomeric forms. Diastereomers may, of course, be separated by conventional means used to separate compounds.

If desired, the racemic mixtures herein may be resolved into their optical antipodes by conventional resolution means; for example by separation (e.g. fractional crystallization) of the diastereomeric salts formed by the reaction of these compounds with optically active acids. Exemplary of such optically active acids are the optically active forms of champhor-10-sulfonic acid, 2-bromo-camphor-$\pi$-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers of the compounds of Formula (I).

Reaction Schemes 1 and 2 have, in common, step (a), the condensation of theobromine with a halide containing the desired side chain. The reaction is carried out in the presence of a polar solvent, such as for example, aqueous alkanol, a pure polar alcohol, polar ketone, or water, preferably aqueous isopropanol, and using a basic catalyst such as, e.g. sodium or potassium hydroxide or carbonate, preferably potassium hydroxide. The reaction is carried out at elevated temperatures of about 70°–120°, most conveniently at the reflux temperature of the solvent. A several-fold molar excess, preferably (2–3 fold) of the halide bearing the side chain, (i.e. the compound of formula X-A), is used.

Compounds of Formula IV are described in European Patent Application No. 79/400.214.7. They are prepared in a manner similar to that described in step (a) for the preparation of compounds of Formula IIa and IIb, but substituting the appropriate phenol or thiophenol for theobromine. As described above, the reaction is carried out in a polar solvent at elevated temperatures with a basic catalyst and, similarly, using a molar excess of the compound of formula X-A over the substrate phenol or thiophenol.

The condensation of the compounds of Formula IV with piperazine to yield compounds of Formula III (step b, reaction scheme 1) and of compounds of Formula II with piperazine to yield compounds of Formula V (step d, reaction scheme 2) are carried out in similar fashion. In each case, an excess of piperazine (about 1.5–4 fold, preferably 2–3 fold molar excess) is heated to reflux with the halide in the presence of a polar solvent such as methyl ethyl ketone (MEK), water, ethanol and the like, preferably alcohol-water. Reaction is continued for about 12–36 hours, preferably 20–25 hours. A basic catalyst, as described above for step (a) is used, in this case, preferably, sodium hydroxide. The resulting piperazine adduct is then isolated by conventional means, known to those skilled in the art.

The condensations represented by steps (c) of scheme 1, and step (e) of scheme 2 are again similar, both to each other and to the steps previously described. The reaction conditions approximate those described above as to solvent, catalyst, time and temperature. However, approximately equimolar amounts of the reactants containing the two ends of the molecule are employed.

The reaction schemes, shown offer methods to prepare all of the compounds of the present invention. However, it should be noted, in addition, that compounds of Formula I wherein $Z_1$ and/or $Z_2$ is C=O may be reduced to the corresponding alcohols of Formula I using a metal hydride, such as, for example, $KBH_4$ or $NaBH_4$ in a polar solvent, such as aqueous methanol. The reduction is accomplished by dissolving the substrate carbonyl in the solvent chosen, and adding an excess (the amount of excess depending on the side reaction with solvent) of the hydride in small portions with stirring until reaction is complete. The temperature is kept at about 0°–25° C., preferably 4°–15° C.

Conversely, compounds of Formula I wherein $Z_1$ and/or $Z_2$ is CHOH may be oxidized to the corresponding carbonyls under suitable, mild conditions. Appropriate oxidizing agents include, for example, dilute neutral permanganate or chromic acid, preferably permanganate. The substrate alcohol is dissolved in a polar solvent such as alcohol, MEK, or alkanol-water, and a solution of the oxidizing agent added until reaction is complete. Approximately stoichiometric amounts of oxidizing agent are required. The temperature is kept at about 5°–30° preferably 15°–20° C.

Also, compounds of Formula I wherein $Z_1$ and/or $Z_2$ is CHOH may be esterified to convert them to the alkanoyl derivatives. This is accomplished by heating the compound of Formula I with a molar excess of the appropriate carboxylic anhydride or chloride in a tertiary amine solvent, such as, for example, pyridine. The temperature is kept at about 20°–90°, preferably 15°–30°.

Conversely, the compounds of Formula I wherein $Z_1$ and/or $Z_2$ is

may be hydrolyzed, using conventional methods, well known to those in the art to the corresponding alcohols: The ester is heated in a water solution with an acid or basic catalyst until hydrolysis is complete.

Salts of the compounds of Formula I are prepared by reacting the corresponding free bases with appropriate acids or acid salts at a temperature of between 0° and 100° C. Conversely, free bases can be prepared by reacting corresponding acid addition salts with suitable alkaline agents, such as sodium or potassium hydroxide at 0°–100° C.

The products of Formula I, synthesized by any of the pathways disclosed herein are optionally converted, when appropriate, to the free base, or to any salt, said salts including, but no being limited to the pharmaceutically acceptable acid addition salts.

Preferred Embodiments

Preferred embodiments of the compounds of the invention are those wherein n and m are 1, and $Z_1$ and $Z_2$ are CHOH or $CH_2$, and the pharmaceutically acceptable acid addition salts thereof.

Especially preferred are the following and their pharmaceutically acceptable acid addition salts:

1-(3-theobromin-1-yl-2-hydroxypropyl)-4-(3-phenylthiopropyl)piperazine.

Utility and Administration

The compounds of the present invention are particularly effective antihistamines. They have been demonstrated to antagonize the effects of histamine in a variety of tests related to such activity, including their activity in prevention of anaphylactic shock in rats, bronchodilation in guniea pigs, inhibition of muscle contraction in response to stress in rats, and brachycardial effects in guinea pigs. Therefore, the compounds are useful in the treatment of respiratory diseases and allergic reactions in mammals, including, but not limited to, asthma, hay fever, and the common cold.

Administration of the active compounds and salts described herein can be via any of the accepted modes of administration for antihistaminic agents which relieve congestion or otherwise effect the control of allergic or other respiratory symptoms. These methods include oral, parenteral and otherwise systemic, or aerosol forms. Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.1–500 µg/kg/day, preferably 5–100 µg/kg/day. For an average 70 kg human, this would amount to 7 µg to 35 mg per day, or preferably 35 µg to 7 mg/day.

Typical compositions contain 0.01–95% by weight of active ingredient, with the balance one or more acceptable non-toxic carriers. The precentage of active ingredient, will, of course, depend upon the dosage form and the mode of administration.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pennsylvania, 15th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkalene glycols or triglycerides. Such suppositories may be formed from mixtures containing active ingredient in the range of 0.5%–10%; preferably 1–2%.

For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates of sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarly propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

EXAMPLES

The following Examples are illustrative of the invention, but are not to be construed as limiting it:

Preparation A

Preparation of 1-(3-Chloropropyl)-Theobromine (Step a, Preparation of IIa)

A well stirred reaction medium containing 1 mole theobromine, 3 moles 1-bromo-3-chloro-propane, 600 ml isopropyl alcohol and 60 ml water is refluxed for 24 hours.

An aqueous solution of potassium hydroxide (1.2 mole) is then slowly added dropwise thereto.

The alcohol solvent is then removed, the resulting material is extracted with methylene chloride, washed with water, after which the solvent is evaporated off, and the product is recrystallized from methanol.

Preparation B

Preparation of 1-(3-Phenylthiopropyl)-Piperazine (Step b, Preparation of III)

To a solution containing 1.1 mole sodium hydroxide in 500 ml water are added 1 mole thiophenol and 2 moles 1-bromo-3-chloro-propane. The mixture is then refluxed for 30 hours, with vigorous stirring. After cooling, the resulting material is extracted with methylene chloride. After washing with dilute lye, and then with water, the solvent is evaporated in vacuo. The chlorinated derivative distills at 138°–140° C. under 13 mm Hg.

To 1 liter 50% aqueous alcohol are added 3 moles pierazine, 1 mole 3-phenylthio-1-chloropropane, 1 mole 10 N sodium hydroxide. The mixture is refluxed for 24 hours, with stirring. The ethanol is then evaporated off, and the resulting material is extracted with methylene chloride. The organic phase is thoroughly washed with water, and is then concentrated and distilled: bp 0.05 mm=140°–142° C.

Preparation C

Preparation of (3-Theobromin-1-yl-2-Hydroxypropyl)Chloride (Step a, Preparation of IIb)

0.20 moles of theobromine is dissolved in 600 ml ethanol, which contains 0.20 moles of sodium hydroxide by stirring at 50° C. The solvent is evaporated and the residue dried.

The above residue is refluxed in 700 ml of epichloro hydrin. The NaCl precipitate is filtered off and the filtrate evaporated to give a residue, which is recrystallized from ethanol to give the title compound.

EXAMPLE 1

Preparation of 1-(3-theobromin-1-yl-2-hydroxypropyl)-4-(3-phenylthiopropyl)piperazine (Step c, Reaction Scheme I)

(3-theobromin-1-yl-2-hydroxypropyl)chloride (1 mole) and 1-(3-phenylthiopropyl)-piperazine are refluxed for 24 hours in a 50% aqueous-alcoholic solution. On completion of the reaction, sodium hydroxide (1 mole) is then added. The mixture is extracted with methylene chloride and washed with water, after which the solvent is evaporated off and the residue is recyrstallized from ethanol.

The dihydrochloride is prepared in the manner described in Example 3, m.p.=226° C.

EXAMPLE 2

7-[3-[4-(3-phenylthiopropyl)-1-piperazinyl]-2-hydroxypropyl]-theobromine (Step e) Reaction Scheme 2)

A solution of ethanol (2 liters) containing 1-(3-theobromine-1-yl-2-hydroxypropyl)piperazine (1 mole) and 3-(phenylthio)propylchloride (1 mole) is refluxed for 5 hours. The ethanol is partly removed, and crystallization takes place. The resulting crystals are suction filtered and may be recrystallized from ethanol.

The dihydrochloride is prepared in the manner described in Example 3, m.p.=234° C.

EXAMPLE 3

Conversion of Free Base to salt.

Excess 3% hydrogen chloride in methanol is added to a solution of 1.0 g 1-(3-theobromin-1-yl-2-hydroxypropyl)-4-(3-phenylthiopropyl)piperazine in 20 ml methanol. Diethyl ether is added until precipitation is complete. The product dihydrochloride is filtered, washed with ether, air dried and recrystallized, m.p. 226° C.

In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, phycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 4

Conversion of Salt to Free Acid.

1.0 g of 1-(3-theobromin-1-yl-2-hydroxypropyl)-4-(3-phenylthiopropyl)piperazine 2 HCl suspended in 50 ml of ether is stirred with excess dilute aqueous potassium carbonate solution until the salt is completely dissolved. The organic layer is then separated, washed twice with water, dried over magnesium sulfate and evaporated to yield 1-(3-theobromin-1-yl-2-hydroxypropyl)-4-(3-phenylthiopropyl)piperazine as the free base.

EXAMPLE 5

Conversion of Alcohol to Ester.

1.0 grams of 1-(3-theobromin-1-yl-2-hydroxypropyl)-4-(3-phenylthiopropyl)piperazine is dissolved in 30 ml pyridine. 2 ml of acetic anhydride is then added. The mixture kept at room temperature for 20 hours. Solvent is evaporated and the ester 1-(3-theobromin-1-yl-2-acetoxypropyl)-4-(3-phenylthiopropyl)piperazine, is then isolated, recrystallized by conventional techniques, as the dihydrochloride.

(B) In a manner similar to that described in part A of this Example, the corresponding n-propionyloxy; i-butyryloxy; n-oxy, and n-caproyloxy valeryl compounds of derived from 1-(3-theobromin-1-yl-2-hydroxypropyl)-4-(3-phenylthiopropyl)piperazine are prepared.

EXAMPLE 6

Other compounds of Formula I may also be prepared according to the procedures of Examples 1 to 5. Exemplary of these are the following compounds for which m=n=1;

| No. | $Z_1$ | Y | $Z_2$ | $R_1$ | $R_2$ | $R_3$ | Nature of the salt | M.P. |
|---|---|---|---|---|---|---|---|---|
| 1 | $CH_2$ | S | $CH_2$ | H | H | H | 2HCl | 234° C. |
| 2 | CHOH | O | $CH_2$ | H | H | H | 2HCl | 234° C. |
| 3 | CHOH | S | $CH_2$ | H | H | H | 2HCl | 226° C. |
| 4 | $CH_2$ | O | $CH_2$ | H | H | H | 2HCl | 224° C. |
| 5 | CHOH | S | $CH_2$ | 4-Cl | H | H | 2HCl | 240° C. |
| 6 | CHOH | O | $CH_2$ | 4-$OCH_3$ | H | H | 2HCl | 250° C. |
| 7 | CHOH | O | $CH_2$ | 4-Cl | H | H | 2HCl | 248° C. |
| 8 | CHOH | O | $CH_2$ | 4-Cl | 3-$CH_3$ | 5-$CH_3$ | 2HCl | 250° C. |
| 9 | CHOH | S | $CH_2$ | 4-$CH_3$ | H | H | 2HCl | 240° C. |
| 10 | $CH_2$ | O | $CH_2$ | 4-Cl | H | H | 2HCl | 250° C. |
| 11 | $CH_2$ | S | $CH_2$ | 4-Cl | H | H | 2HCl | 235° C. |
| 12 | $CH_2$ | S | $CH_2$ | 4-$CH_3$ | H | H | 2HCl | 230° C. |
| 13 | $CH_2$ | S | CHOH | H | H | H | 2HCl | 245° C. |

EXAMPLE 7

Pharmaceutical Compositions

The active ingredient in this example is 1-(3-theobromin-1-yl-2-hydroxypropyl)-4-(3-phenylthiopropyl)piperazine. The other compounds of this invention may, of course, also be used.

| A. CAPSULES | |
|---|---|
| Active Ingredient | 30.0 mg |
| Lactose, special | 163.0 mg |
| Talc | 5.0 mg |
| Magnesium stearate | 2.0 mg |
| B. INJECTABLE AMPOULES | |
| Active Ingredient | 10.0 mg |
| Sodium chloride | 35.0 mg |
| Monosodium phosphate, to pH 5.5–6 | |
| Distilled water, qs ad | 5.0 ml |
| C. TABLETS | |
| Active Ingredient | 10.0 mg |
| Lactose | 80.0 mg |
| Cellulose | 97.5 mg |
| Silica | 1.5 mg |
| Starch | 10.0 mg |
| Magnesium stearate | 1.0 mg |
| D. DRINKABLE SUSPENSION | |
| Active Ingredient | 200.0 mg |
| Benzoic acid | 250.0 mg |
| Polyoxyethylene glycol and water, qs ad | 200.0 ml |
| E. AEROSOL I | |
| Active Ingredient | 0.6% |
| Span 85 | 0.5% |
| Freon 11 | 20.0% |
| Freon 12/Freon 114 (20/80) | 78.9% |
| AERSOL II | |
| Active Ingredient | 0.88% |
| Sodium sulfate (anhydrous), micronized | 0.88% |
| Span 85 | 1.00% |
| Propellant consisting of 50% Freon 12, 25% Freon 11, and 25% Freon 114 | 97.24% |
| AEROSOL III | |
| Active Ingredient | 0.50% |
| Span 80 | 0.50% |
| Propellant (C) consisting of 30% Freon 11 and 70% Freon W | 99.0% |
| AEROSOL IV | |
| Active Ingredient | 3.0% |
| Span 85 (sorbitan trioleate) | 1.0% |
| Freon 11 (trichloromonofluoromethane) | 30.0% |
| Freon 114 (dichlorotetrafluoroethane) | 41.0% |
| Freon 12 (dichlorodifluoromethane) | 25.0% |

What is claimed is:

1. A compound of the formula

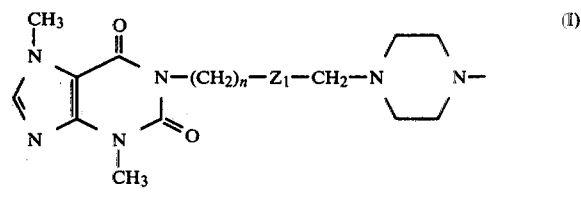

and the pharmaceutically acceptable acid addition salts thereof, wherein
$Z_1$ and $Z_2$ are each independently selected from the group consisting of $CH_2$, CHOB and C=O, wherein B is selected from the group consisting of hydrogen and alkanoyl;
Y is oxygen or sulfur;
n is an integer from 0–4 but cannot be zero when $Z_1$ is CHOB;
m is an integer from 1–4 but cannot be zero when $Z_2$ is CHOB; and
$R_1$, $R_2$ and $R_3$ are each independently hydrogen, halogen, hydroxy, trifluoromethyl, alkyl or alkoxy.

2. The compound of claim 1 and the pharmaceutically acceptable acid addition salts thereof wherein $Z_1$ and $Z_2$ are each independently $CH_2$ or CHOH; and m and n are both 1.

3. The compound of claim 2 and the pharmaceutically acceptable acid addition salts thereof whih is 1-(3-theobromin-1-yl-2-hydroxypropyl)-4-(3-phenylthiopropyl)piperazine.

4. A composition for the treatment of respiratory diseases in mammals which comprises an effective amount of the compound of claim 1 or a pharmaceutically acceptable acid addition salt thereof, in admixture with at least one pharmaceutically acceptable, non-toxic excipient.

5. A method for treating respiratory diseases in mammals, which method comprises administering to a subject in need of such treatment, an effective amount of, or a pharmaceutical composition containing an effective amount of a compound of claim 1 or a pharmaceutically acceptable acid addition salt thereof.

6. A compound of the formula

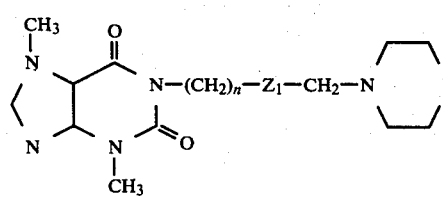 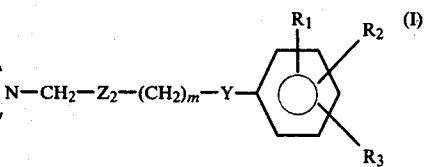

and the pharmaceutically acceptable acid addition salts thereof, wherein
$Z_1$ is selected from the group consisting of $CH_2$, CHOB and C=O, wherein B is selected from the group consisting of hydrogen and alkanoyl;
$Z_2$ is $CH_2$ or CHOB;
Y is oxygen or sulfur;
n is an integer from 0–4 but cannot be zero when $Z_1$ is CHOB;
m is an integer from 0–4 but cannot be zero when $Z_2$ is CHOB; and
$R_1$, $R_2$ and $R_3$ are each independently hydrogen, halogen, hydroxy, trifluoromethyl, alkyl or alkoxy.

7. The compound of claim 6 wherein $Z_1$ and $Z_2$ are each independently $CH_2$ or CHOB.

* * * * *